United States Patent
Berndorfer et al.

(10) Patent No.: US 6,575,018 B2
(45) Date of Patent: Jun. 10, 2003

(54) METHOD FOR DETERMINING OIL VISCOSITY

(75) Inventors: Axel H Berndorfer, El Paso, TX (US); Jim H Campbell, El Paso, TX (US); Amiyo K. Basu, El Paso, TX (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 09/900,788

(22) Filed: Jul. 6, 2001

(65) Prior Publication Data
US 2003/0005751 A1 Jan. 9, 2003

(51) Int. Cl.$^7$ .............................................. G01N 11/00
(52) U.S. Cl. ...................................... 73/54.01; 73/54.02
(58) Field of Search ............................ 73/54.01, 54.02, 73/54.25

(56) References Cited

U.S. PATENT DOCUMENTS

| 4,735,227 A | * | 4/1988 | Royse et al. ............... 73/54.01 |
| 4,796,204 A | * | 1/1989 | Inoue ........................ 73/117.3 |
| 4,815,431 A | * | 3/1989 | Yorita et al. ........... 123/196 AB |
| 5,095,710 A | * | 3/1992 | Black et al. .............. 73/54.28 |
| 5,307,865 A | * | 5/1994 | Inagaki et al. ......... 123/196 AB |
| 5,750,887 A | * | 5/1998 | Schricker .................. 73/117.3 |
| 5,973,503 A | * | 10/1999 | Kuipers et al. ............. 324/698 |
| 6,149,824 A | * | 11/2000 | Chace et al. ................ 210/779 |

FOREIGN PATENT DOCUMENTS

| DE | 4119437 | * | 12/1992 | ................ 73/54.01 |
| DE | 19930684 | * | 1/2001 | ................ 73/54.02 |
| DE | 10055420 | * | 5/2002 | ................ 73/54.02 |

* cited by examiner

Primary Examiner—Daniel S. Larkin
(74) Attorney, Agent, or Firm—Margaret A. Dobrowitsky

(57) ABSTRACT

A method for determining oil viscosity includes measuring an oil viscosity parameter value while an oil pump pumps oil through an engine lubrication system. Thereafter, the oil viscosity parameter value is compared to a stored look-up table of oil viscosity parameter values versus oil viscosity values and the viscosity of the oil contained within the vehicle lubrication system is interpolated from the table. The look-up table is generated by installing the pump in a test system and then, measuring the oil viscosity parameter value as the pump pumps oils of known viscosities. For increased accuracy, the look-up table is generated for several temperatures within the range of normal engine operating temperatures and several pump speeds within the range of normal operating pump speeds.

21 Claims, 3 Drawing Sheets

METHOD FOR DETERMINING OIL VISCOSITY

TECHNICAL FIELD

The present invention relates generally to oil quality sensors.

BACKGROUND OF THE INVENTION

In order to prolong the life of a combustion engine, the oil which provides lubrication to the vital components within the engine must be changed before its viscosity breaks down. If the viscosity of the oil falls outside a predetermined operating range, part-to-part contact can occur and cause catastrophic failure of the engine, i.e., without proper lubrication moving parts within the engine can experience excessive wear causing the engine to become damaged.

Most oil changes today are conducted based on schedules recommended by manufacturers of the vehicles. Due to customer desire, the intervals between oil changes are getting longer. Longer intervals reduce pollution associated with the disposal of waste oil. Similarly, reducing unnecessary oil changes helps minimize pollution due to waste oil. Unfortunately, the useful life of oil, i.e., the viscosity, varies greatly depending on the quality of the oil, the age of the oil, and the operating temperature of the oil. Moreover, contamination of the oil by antifreeze or water can severely impact the oil viscosity.

As a result, the interval between oil changes may exceed the useful life of the oil and thus, it is necessary to monitor the viscosity of the oil between changes to ensure that the oil is still providing the necessary lubrication. If the viscosity of the oil deteriorates, the oil can be changed before the recommended time so that the engine will not be harmed.

Currently, there does not exist an onboard method by which the oil viscosity can relatively easily be determined. On the contrary, oil samples must be taken at certain intervals and analyzed in labs to determine the viscosity of the oil.

The present invention has recognized these prior art drawbacks, and has provided the below-disclosed solutions to one or more of the prior art deficiencies.

SUMMARY OF THE INVENTION

A method for determining oil viscosity in an engine lubrication system includes measuring an oil viscosity parameter value and then, determining the oil viscosity based thereon. Preferably, the engine lubrication system includes an engine and the oil viscosity parameter is measured while the engine is running. If an electric oil pump is used to pump oil to the engine, the oil viscosity parameter may be measured after the engine is shut down. In a preferred embodiment, the method includes generating a look-up table of oil viscosity parameter values versus viscosity values. Thereafter, the oil viscosity parameter value is compared to the look-up table in order to determine the oil viscosity. Preferably, the look-up table includes oil viscosity parameter values versus viscosity values for a range of temperatures. If the oil viscosity falls outside a predetermined operating range, a signal is sent to an output device.

In a preferred embodiment, the oil viscosity parameter value is a power consumption value of an oil pump. The look-up table that is generated includes power consumption values versus viscosity values. The power consumption value is compared to the look-up table in order to determine the oil viscosity. If a mechanical oil pump is used to pump oil to the engine, the power consumption value is determined based on a signal from a torque sensor that is mechanically coupled to the oil pump. On the other hand, if an electric oil pump is used to pump oil to the engine, the power consumption value is determined by measuring the power consumed by the pump motor.

In another aspect of the present invention, the oil viscosity parameter value is measured while pumping the oil through a bypass with the engine off. Preferably, the bypass is a calibrated capillary within the pump. In this aspect of the present invention, a look-up table is generated and includes power consumption values while the pump is pumping through the bypass.

In yet another aspect of the present invention, an engine lubrication system includes an engine and an oil pan. A pump communicates with the engine and the oil pan. The system also includes a control module that has logic means for receiving a signal that represents an oil viscosity parameter value. Moreover, the control module includes logic means for determining oil viscosity based thereon.

The present invention will now be described, by way of example, with reference to the accompanying drawings, in which:

DESCRIPTION OF AN EMBODIMENT OF THE INVENTION

Figure 1:
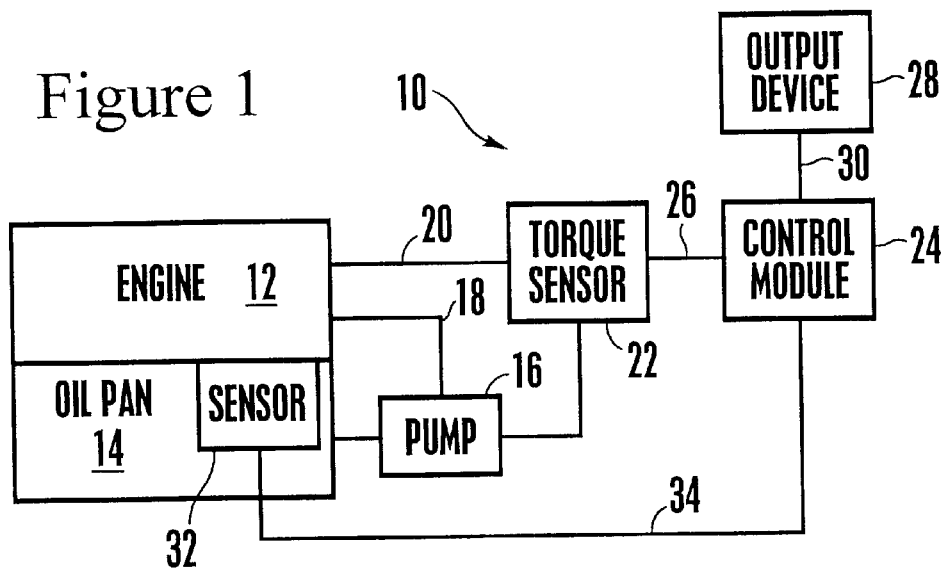
FIG. 1 is a block diagram of an engine lubrication system having a mechanical oil pump.

Referring initially to FIG. 1, an engine lubrication system is shown and generally designated 10. FIG. 1 shows that the lubrication system includes an engine 12 and an oil reservoir, e.g., an oil pan 14, in fluid communication with the engine 12. As shown in FIG. 1, an oil pump 16 is in fluid communication with the engine 12 and the oil pan 14 and pumps oil from the oil pan 14 to the engine 12, via a fluid line 18, in order to lubricate moving parts within the engine 12, e.g., the crankshaft, pistons, valves, rocker arms, push rods, and cam shafts.

FIG. 1 shows a mechanical connection 20 between the engine 12 and the oil pump 16, e.g., a first sprocket attached to an engine crank shaft, a second sprocket attached to a pump shaft, and a chain installed there around. Thus, when the engine 12 is running, it drives the oil pump 16 in order to draw the oil from the oil pan 14 and pump it to the engine 12. As shown in FIG. 1, a torque sensor 22 is incorporated in the mechanical connection 20 between the engine 12 and the oil pump 16. A control module 24, e.g., an engine control module (ECM) or a body control module (BCM), is connected to the torque sensor 22 via an electrical line 26. An output device 28 is connected to the control module 24 via electrical line 30. Optionally, an oil sensor 32, that can be disposed in the oil pan 14, is connected to the control module 24 via electrical line 34. It is to be appreciated that the output device 28 can be an audible warning device, e.g., a buzzer or audible alarm. The output device 28 can also be a visual warning device, e.g., a warning lamp or other visual display. Or, the output device 28 can be a visual indicator of the oil viscosity, e.g., a gauge or similar device.

Figure 2:
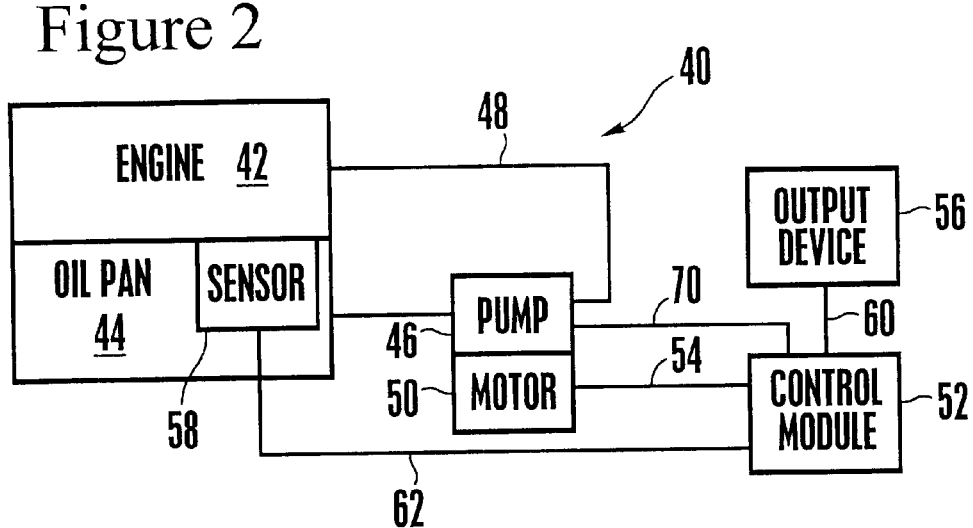
FIG. 2 is a block diagram of an engine lubrication system having an electric oil pump.

FIG. 2 shows an alternative engine lubrication system that is generally designated 40. As shown in FIG. 2, this system includes an engine 42 and an oil reservoir, e.g., an oil pan 44, in fluid communication with the engine 42. An electric oil pump 46 is in fluid communication with the engine 42 and the oil pan 44 and pumps oil from the oil pan 44 to the engine 42 via a fluid line 48.

As shown in FIG. 2, an electric pump motor 50 is coupled to the pump 46 and drives the pump 46 in order to draw the oil from the oil pan 44 and pump it to the engine 42. A control module 52, is connected to the motor 50 via an electrical line 54. FIG. 2 further shows an output device 56 and an oil sensor 58 that are connected to the control module 52 via electrical line 60 and electrical line 62, respectively.

Figure 3:
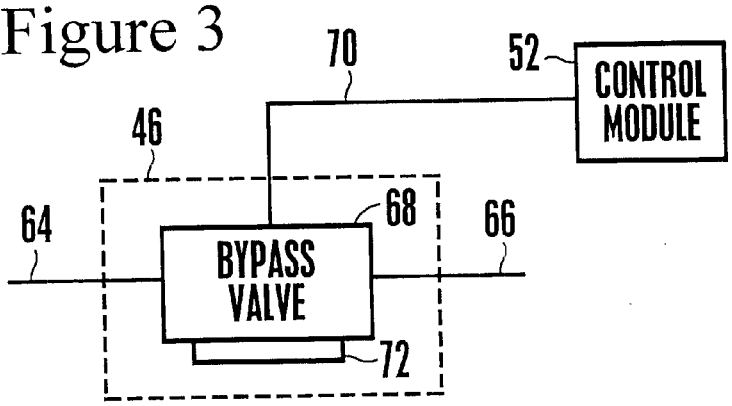
FIG. 3 is a block diagram of an oil pump having an internal bypass.

FIG. 3 shows a detailed view of the electric oil pump 46, described above. FIG. 3 shows that the electric oil pump 46 has an inlet 64 and an outlet 66 that allows the pump 46 to provide fluid communication between the oil pan 44 and the engine 42, described above. Within the pump 46, is a bypass valve 68, e.g., a solenoid valve, that is connected to the control module 52 via electrical line 70. When energized, the bypass valve 68 shunts oil through a calibrated capillary 72. As described in detail below, while the oil is pumped through the calibrated capillary 72, the power consumption of the motor 50 is measured. Preferably, the calibrated capillary 72 is within the oil pump 46. It is to be appreciated that a calibrated orifice can be used in lieu of the calibrated capillary 72.

While the preferred implementation of either control module 24, 52 is an onboard chip, such as a digital signal processor, it is to be understood that the logic disclosed below can be executed by other digital processors, such as by a personal computer. Or, the control module 24, 52 may be any computer, including a Unix computer, or OS/2 server, or Windows NT server, or a laptop computer. In the case of a "smart" oil quality sensor, the logic can be executed by a processor within the sensor.

The control module 24, 52 includes a series of computer-executable instructions, as described below, which will allow the control module 24, 52 to determine the viscosity of the oil contained in the lubrication system based on a power consumption value of the pump 16, 46. These instructions may reside, for example, in RAM of the control module 24, 52.

Alternatively, the instructions may be contained on a data storage device with a computer readable medium, such as a computer diskette. Or, the instructions may be stored on a DASD array, magnetic tape, conventional hard disk drive, electronic read-only memory, optical storage device, or other appropriate data storage device. In an illustrative embodiment of the invention, the computer-executable instructions may be lines of compiled C++ compatible code.

The flow charts herein illustrate the structure of the logic of the present invention as embodied in computer program software. Those skilled in the art will appreciate that the flow charts illustrate the structures of computer program code elements including logic circuits on an integrated circuit, that function according to this invention. Manifestly, the invention is practiced in its essential embodiment by a machine component that renders the program elements in a form that instructs a digital processing apparatus (that is, a computer) to perform a sequence of function steps corresponding to those shown.

Figure 4:
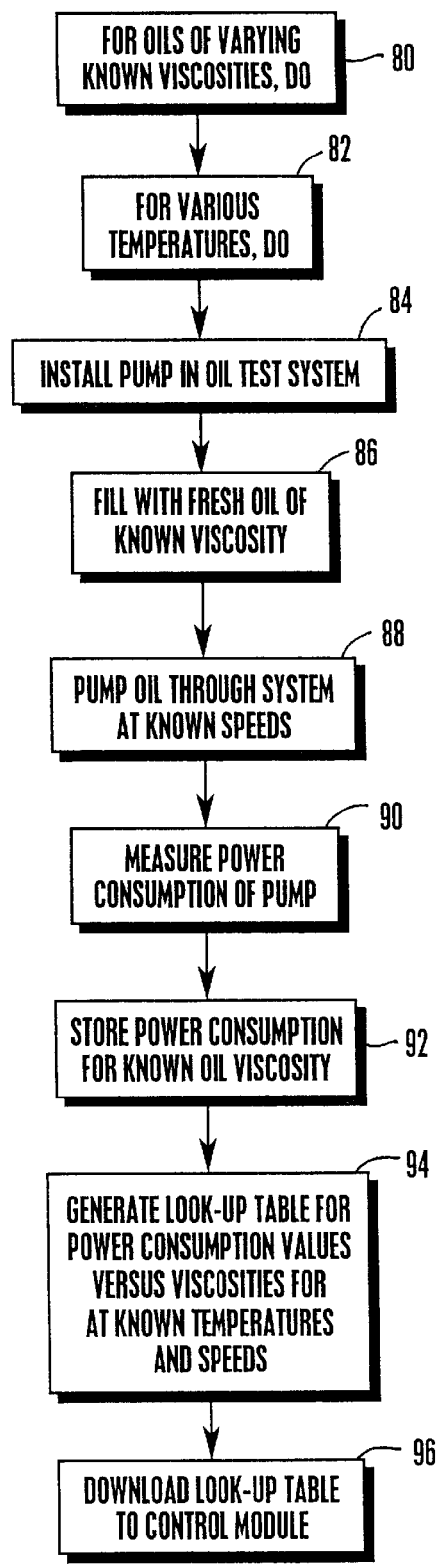
FIG. 4 is a flow chart of the calibration logic.

Referring to FIG. 4, calibration logic of the present invention is shown. Commencing at block 80, a do loop is entered wherein the succeeding steps are performed for oils of varying known viscosities. Moving to block 82, a second do loop is entered wherein the succeeding steps are performed over several temperatures spanning the range of normal engine operation temperatures.

As shown in FIG. 4, at block 84, the oil pump 16, 46 is installed in an oil test system. Thereafter, at block 86, the test system is filled with fluid that in a preferred embodiment is fresh oil having a known viscosity. Then, the logic proceeds to block 88 where oil is pumped through the test system using the oil pump 16, 46 at various pump speeds. At block 90, while oil is being pumped through the test system, the power consumption of the pump 16, 46 is measured for each pump speed. If the mechanical pump 16 is installed in the test system, the power consumption of the pump is determined by utilizing a torque sensor mechanically coupled to the pump. On the other hand, if the electric pump 46 is installed in the test system, the power consumption is determined directly from the power consumed by the pump motor 50.

Continuing to block 92, the power consumption values of the pump 16, 46 while pumping the oil of known viscosity at different pump speeds are stored. At block 94, a lookup table is generated for power consumption values versus viscosity curves obtained at several temperatures spanning the range of normal engine operation temperatures and at several pump speeds spanning the range of normal pump operating speeds. Moving to block 96, the lookup table is downloaded to the control module 24, 52 in the vehicle lubrication system 10, 40 for use in the operation logic described below. It is to be appreciated that the oil pump speed (rpm), the engine speed (rpm), ambient temperature, and coolant temperature can alter the temperature of the oil and thus, alter the viscosity of the oil. Accordingly, these parameters can be accounted for, e.g., by increasing the temperature range for which the look-up tables are generated or by generating the look-up tables at different oil pump speeds.

Figure 5:
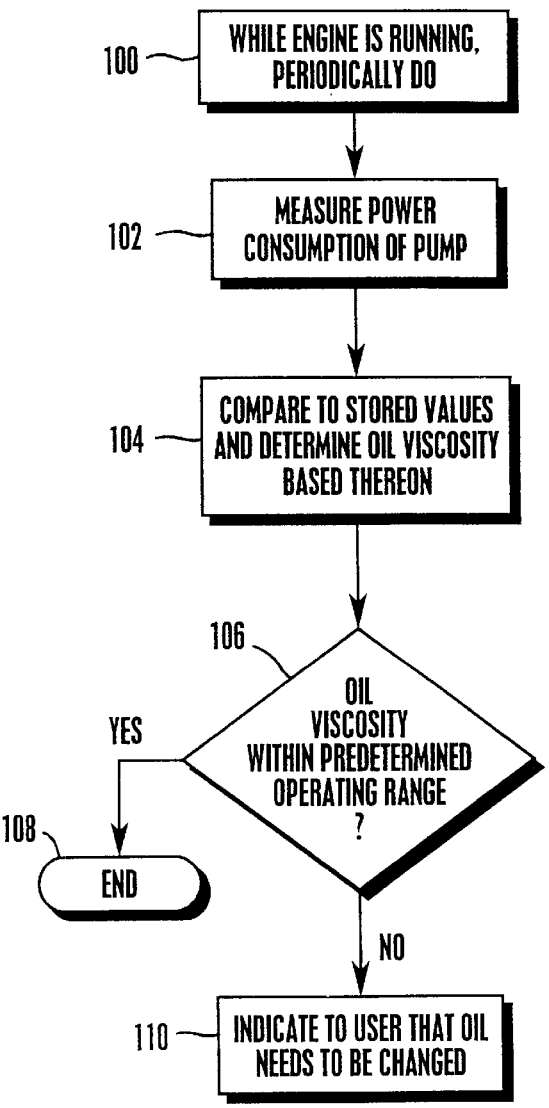
FIG. 5 is a flow chart of the operating logic.

Now referring to FIG. 5, the operation logic of the present invention is shown and commences at block 100 with a do loop wherein while the engine is running the succeeding steps are periodically performed. It is to be understood that in the vehicle lubrication system 40 in which the electric oil pump 46 is utilized, it is preferred that the succeeding steps be performed while the engine 42 is turned off. Proceeding to block 102, the power consumption of the pump 16, 46 is measured while the pump 16, 46 is pumping oil through the vehicle lubrication system 10, 40. As described above, the power consumed by the electric pump 46 is determined directly from the pump motor 50. On the other hand, the power consumed by the mechanical pump 16 is determined using the torque sensor 22 incorporated in the mechanical connection between the engine 12 and the pump 16.

Continuing the description of the logic, at block 104 the power consumption value measured at block 102, is compared to values stored in the control module 24, 52, e.g., the look up table generated above. The oil viscosity is then interpolated from the look up table. Moving to decision diamond 106, it is determined whether the oil viscosity is within a predetermined operation range. If so, the logic ends at state 108. However, if the oil viscosity is not within the predetermined operating range, the logic moves to block 110 where the control module 24, 52 sends a signal to the output device 28, 56 in order to indicate to the user that the oil in the vehicle lubrication system 10, 40 needs to be changed.

It is to be appreciated that the operating range of the oil viscosity can be determined as described below in conjunction with FIG. 8. On the other hand, the operating range can be predetermined by the manufacturer of the vehicle. If so, since the operating range typically varies based on the ambient conditions in which the vehicle is operated, the user can be advised to change the oil to an oil of proper viscosity based on the ambient conditions where the vehicle is operated. It is also to be appreciated that the logic shown in FIG. 5 and described above can be performed for the electric pump 46 when the engine is not running. If so, it is preferable to follow logic steps 102 through 110 immediately after the engine is shut down upon reaching a temperature within the normal range of operating temperatures.

Figures 6, 7, 8:
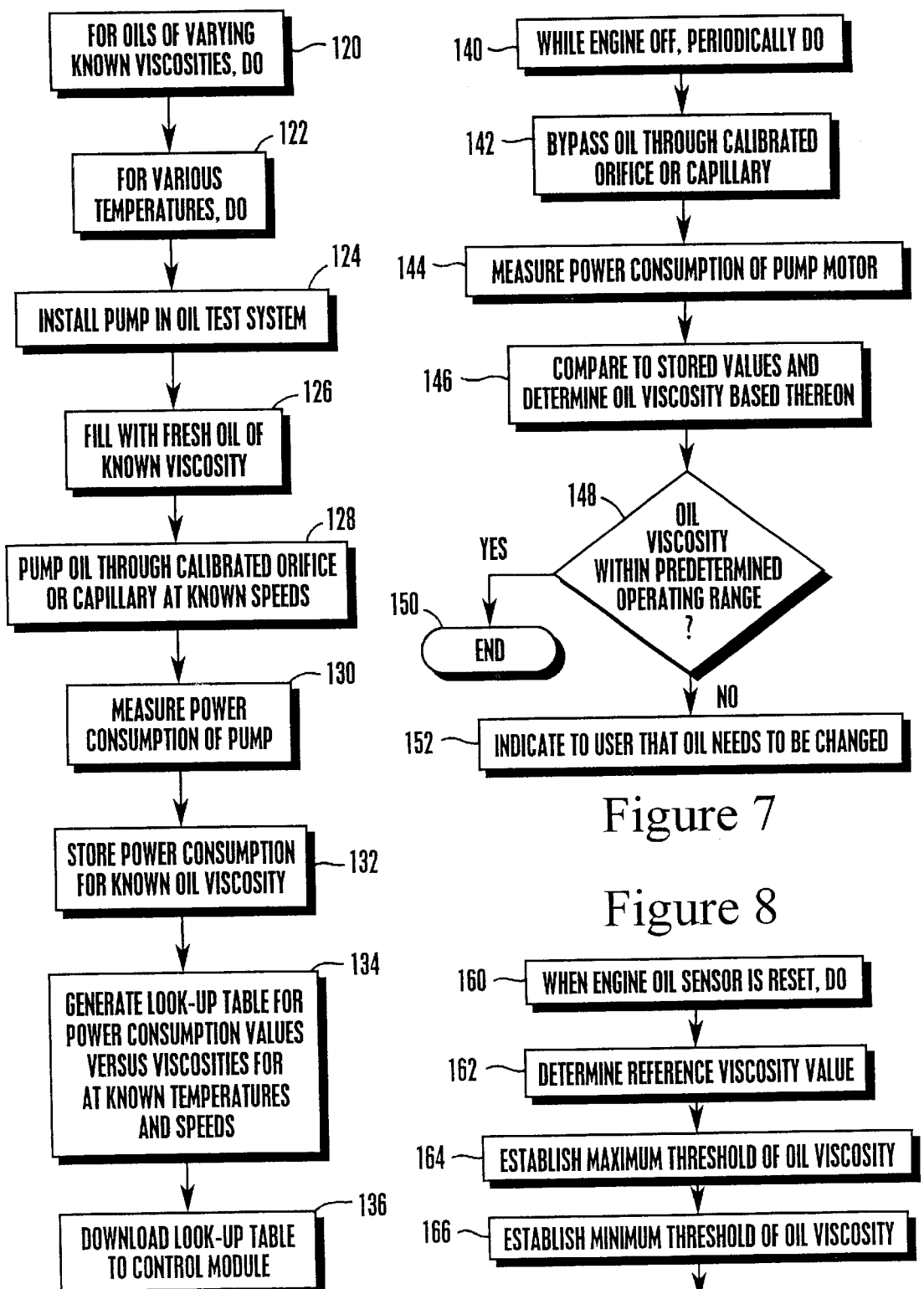
FIG. 6 is a flow chart of alternative calibration logic.
FIG. 7 is a flow chart of alternative operating logic.
FIG. 8 is a flow chart of the logic for establishing relative viscosity operating range values.

Referring to FIG. 6, alternative calibration logic of the present invention is shown. It is to be appreciated that the calibration logic shown in FIG. 6 is for the electric oil pump 46 only. Commencing at block 120, a do loop is entered wherein the succeeding steps are performed for oils of varying known viscosities. Moving to block 122, a second do loop is entered wherein the succeeding steps are performed over several temperatures spanning the range of normal engine operation temperatures.

As shown in FIG. 6, at block 124, the electric oil pump 46 is installed in an oil test system. Thereafter, at block 126, the test system is filled with fresh oil having a known viscosity. Then, the logic proceeds to block 128 where oil is pumped through the calibrated capillary 72 at various speeds. At block 130, while oil is being pumped through the calibrated capillary 72, the power consumption of the pump 46 at the various speeds is measured. Continuing to block 132, the power consumption values determined while the oil is pumped through the calibrated capillary 72 are stored. At block 134, a lookup table is generated for flow rates versus viscosity curves obtained at several temperatures spanning the range of normal engine operation temperatures and at several pump speeds spanning the range of normal pump operating speeds. Moving to block 136, the lookup table is downloaded to the control module 52 in the vehicle lubrication system 40 for use in conjunction with the operation logic described below.

Now referring to FIG. 7, alternative operation logic of the present invention, for use in conjunction with the electric oil pump 46 only, is shown and commences at block 140 with a do loop wherein while the engine is off the succeeding steps are periodically performed. Proceeding to block 142, oil is bypassed through the calibrated capillary 72. At block 144, while oil is pumped through the calibrated capillary 72, the power consumption of the pump motor 50 is measured. Continuing to block 146, the power consumption of the pump motor 50 measured at block 144 is compared to values stored in the control module 52, e.g., the look up table generated above. The oil viscosity is then interpolated from the look up table. Moving to decision diamond 148, it is determined whether the oil viscosity is within a predetermined operation range. If so, the logic ends at state 150. However, if the oil viscosity is not within the predetermined operating range, the logic proceeds to block 152 where the control module 52 sends a signal to the output device 56 in order to indicate to the user that the oil in the vehicle lubrication system 40 needs to be changed.

It is to be appreciated that bypassing the oil flow from the engine lubrication system to the calibrated capillary 72 and then, measuring the power consumption of the pump motor 50 eliminates the variations in oil flow through the engine lubrication system caused, e.g., by engine tolerances, lubricating system tolerances, operating conditions, and wear. Thus, measuring the power consumption while the oil flows through the calibrated capillary increases the accuracy of the measurement.

Referring to FIG. 8, logic for determining the operating range of the oil viscosity is shown. Commencing at block 160 a do loop is entered wherein when the oil sensor 32, 58 is reset by the control module 24, 52, the following steps are performed. At block 162, a reference viscosity value of the fresh oil is determined using one of the methods described above. Moving to block 164, a maximum threshold for the operating range of the oil viscosity is established based on the reference value. For example, the maximum threshold can be established at a fifty percent increase from the reference value. Continuing to block 166, a minimum threshold for the operating range of the oil viscosity is established based on the reference value. The minimum threshold can be established, for example, at a fifty percent decrease from the reference value measured at block 162. Thereafter, the logic ends at state 168.

With the configuration of structure and logic described above, it is to be appreciated that the method for determining oil viscosity can be used to determine the viscosity of oil in a vehicle lubrication system 10, 40 without having to take a sample of the oil and send it to a laboratory.

While the particular METHOD FOR DETERMINING OIL VISCOSITY as herein shown and described in detail is fully capable of attaining the above-described objects of the invention, it is to be understood that it is the presently preferred embodiment of the present invention and thus, is representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it is to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. section 112, sixth paragraph, unless the element is expressly recited using the phrase "means for."

We claim:

1. A method for determining oil viscosity in a vehicle lubrication system, comprising the acts of:
   measuring an oil pump power consumption value; and
   determining the oil viscosity at least partially based thereon.

2. The method of claim 1, wherein vehicle lubrication system includes an engine and the oil pump power consumption value is measured while the engine is running.

3. The method of claim 1, wherein the vehicle lubrication system includes an engine and an electrically driven oil pump and the oil pump power consumption value is measured when the engine is off.

4. The method of claim 1, further comprising the act of:
generating a look-up table of oil viscosity parameter values versus viscosity values.

5. The method of claim 4, further comprising the acts of:
comparing the oil viscosity parameter value to the look-up table; and
determining the oil viscosity at least partially based thereon.

6. The method of claim 4, wherein the look-up table includes oil viscosity parameter values versus viscosity values for a range of temperatures.

7. The method of claim 1, further comprising the act of:
sending a signal to an output device when the oil viscosity falls outside a predetermined operating range.

8. The method of claim 1, further comprising the acts of:
generating a look-up table of oil pump power consumption values versus viscosity values;
comparing the oil pump power consumption value to the look-up table; and
determining the oil viscosity at least partially based thereon.

9. The method of claim 1, wherein the oil pump is a mechanically driven oil pump and the oil pump power consumption value is determined based at least partially on a signal from a torque sensor mechanically coupled to the oil pump.

10. The method of claim 1, wherein the oil pump is an electrically driven oil pump and the oil pump power consumption value is determined by measuring the power consumed by a pump motor.

11. The method of claim 10, wherein the power consumed by the pump motor is measured while pumping oil through a bypass.

12. The method of claim 11, wherein the bypass is a calibrated capillary within the oil pump.

13. A vehicle lubrication system, comprising:
an engine;
an oil pan;
a pump communicating with the engine and the oil pan; and
a control module including logic means for receiving a signal representing an oil pump power consumption value and logic means for determining oil viscosity at least partially based thereon.

14. The system of claim 13, wherein the control module further includes:
a look-up table stored therein, the look-up table including oil pump power consumption values versus viscosity values;
logic means for comparing the oil pump power consumption value to the look-up table; and
logic means for determining the oil viscosity at least partially based thereon.

15. The system of claim 14, wherein the look-up table includes oil pump power consumption values versus viscosity values for a range of temperatures.

16. The system of claim 13, wherein the system further includes an output device electrically connected to the control module.

17. The system of claim 16, wherein the control module further comprises:
logic means for sending a signal to the output device when the oil viscosity falls outside a predetermined operating range.

18. The system of claim 13, wherein the oil pump is a mechanically driven oil pump and the oil pump power consumption value is determined based at least partially on a signal from a torque sensor mechanically coupled to the oil pump.

19. The system of claim 13, wherein the oil pump is an electrically driven oil pump and the oil pump power consumption value is determined by measuring the power consumed by an electric pump motor connected to the pump.

20. The system of claim 13, further comprising a bypass and the oil pump power consumption value is measured while pumping oil through the bypass.

21. The system of claim 20, wherein the bypass is a calibrated capillary within the oil pump.

* * * * *